(12) United States Patent
Chung et al.

(10) Patent No.: US 7,876,940 B2
(45) Date of Patent: Jan. 25, 2011

(54) UNIVERSAL IMAGE PROCESSING

(75) Inventors: William Hyun-Kee Chung, Cortlandt Manor, NY (US); Bruce A. Foster, Dunstable, MA (US); Moon J. Kim, Wappingers Falls, NY (US); James R. Moulic, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 890 days.

(21) Appl. No.: 11/668,875

(22) Filed: Jan. 30, 2007

(65) Prior Publication Data
US 2008/0181471 A1 Jul. 31, 2008

(51) Int. Cl.
*G06K 9/00* (2006.01)
(52) U.S. Cl. .................. 382/128; 382/115; 382/100
(58) Field of Classification Search .......... 382/115, 382/118, 128, 233, 100; 375/E7.026, E7.089; 704/E19.009, E17.112
See application file for complete search history.

(56) References Cited

U.S. PATENT DOCUMENTS

| | | |
|---|---|---|
| 6,404,902 B1 | 6/2002 | Takano et al. |
| 6,567,622 B2 | 5/2003 | Phillips |
| 6,661,931 B1 | 12/2003 | Kawada |
| 6,744,931 B2 | 6/2004 | Komiya et al. |
| 6,829,378 B2 | 12/2004 | DiFilippo et al. |
| 7,095,882 B2 | 8/2006 | Akahori |
| 7,102,777 B2 | 9/2006 | Haraguchi |
| 7,142,725 B2 | 11/2006 | Komiya et al. |
| 2002/0164059 A1 | 11/2002 | DiFilippo et al. |
| 2002/0198371 A1 | 12/2002 | Wang |
| 2003/0031355 A1 | 2/2003 | Nagatsuka |
| 2003/0092980 A1 | 5/2003 | Nitz |
| 2003/0113034 A1 | 6/2003 | Komiya et al. |
| 2004/0062454 A1 | 4/2004 | Komiya et al. |
| 2004/0122790 A1 | 6/2004 | Walker et al. |
| 2004/0186371 A1 | 9/2004 | Toda |
| 2005/0113960 A1 | 5/2005 | Karau et al. |
| 2005/0263678 A1 | 12/2005 | Arakawa |
| 2006/0250514 A1 | 11/2006 | Inoue et al. |
| 2006/0268357 A1 | 11/2006 | Vook et al. |

FOREIGN PATENT DOCUMENTS

WO 2008092744 A2 8/2008

OTHER PUBLICATIONS

Patent Cooperation Treaty, PCT/EP2008/050443, PCT International Preliminary Report on Patentability and Written Opinion of the International Searching Authority dated Aug. 4, 2009, 8 pages.
Kuhnen, Leila, "Invitation to Pay Additional Fees - Communication Relating to the Results of the Partial International Search", PCT International Searching Authority, Apr. 25, 2008.
Patent Cooperation Treaty, PCT/EP2008/050443, PCT International Search Report dated Jul. 22, 2008, 7 pages.

*Primary Examiner*—Anh Hong Do
(74) *Attorney, Agent, or Firm*—William E. Schiesser; Hoffman Warnick LLC (57) ABSTRACT

The present invention provides a universal and centralized image (e.g., medical, bio-molecular, etc.) processing system platform. The invention permits sharing both computation and visualization across a single universal platform, thus allowing for sharing of computing resources and visualization of images on a variety of imaging (client) devices without high-performance graphical display cards. In a typical embodiment a (e.g., medical) image 2D linear registration algorithm is implemented on a Cell Broadband Engine processor, which has nine processor cores on a chip and has a 4-way SIMD unit for each core.

20 Claims, 8 Drawing Sheets

1. MODALITY SELECTION SETTINGS LOADED FROM OPERATOR OR PROFILE
2. SPECIFIC TEST MODALITY CHOSEN
3. CORRESPONDING SENSOR ELEMENTS ACTIVATED TO SUPPORT SELECTED MODALITY
4. SENSOR ELEMENT SETTINGS PROFILE OR DYNAMIC RECONFIGURATION SETTINGS FROM ANALYSIS AND OPTIMIZATION BLOCK
5. & 6. TARGET POSITIONING (LOCATION, ORIENTATION AND INCREMENTAL MOTION) LOADED
7. & 8. SENSOR ELEMENT POSITIONING (LOCATION, ORIENTATION AND RESOLUTION) LOADED
9. DATA ACQUISITION INITIATED
10. COLLECTED DATA SENT ON TO FILTERING, PRE-PROCESSING
REPEATING STEPS 4 - 10 WILL OCCUR OF REAL-TIME RECONFIGURATION OF TARGET AND SENSOR ELEMENT SETTINGS

UNIVERSAL IMAGE PROCESSING

FIELD OF THE INVENTION

This invention generally relates to image processing. Specifically, the present invention provides a universal and central image processing method, system, and program product.

BACKGROUND OF THE INVENTION

Modern day medical and biomolecular imaging scanners can generate large amounts of data in a short period of time, usually requiring a dedicated computer for processing and visualization. For indirect medical imaging modalities/devices, such as MRI, PET and CT, the raw data, commonly called k-space data, needs to be mathematically transformed into images which require super scale computing power. This process, called image reconstruction, can take hours using current desktop x86 or Macintosh systems and severely limits clinical use of medial imaging applications. Unfortunately, current solutions use a dedicated imaging processing system for a single modality, making inefficient use of computing resources.

Recent advances in multi-core computer processor technology will drastically reduce image processing time. It will also open the door to new possibilities of sharing computer intensive processors among the modalities. Emerging multi-core processors are able to accelerate medical imaging applications by exploiting the parallelism available in their algorithms. Unfortunately all existing systems require a separate processing system for each imaging device, which is both costly and decentralized.

SUMMARY OF THE INVENTION

In general, the present invention provides a universal and centralized image (e.g., medical, bio-molecular, etc.) processing system platform. The invention permits sharing both computation and visualization across a single universal platform, thus allowing for sharing of computing resources and visualization of images on a variety of imaging (client) devices without high-performance graphical display cards. In a typical embodiment, a (e.g., medical) image 2D linear registration algorithm is implemented on a Cell Broadband Engine processor, which has nine processor cores on a chip and has a 4-way SIMD unit for each core.

By exploiting a highly parallel architecture and a high memory bandwidth of the Cell Broadband Engine architecture, this implementation with two Cell Broadband Engine processors can compute mutual information for about 33 million pixel pairs in a second. This technological advancement allows for the development of an image processing system that can be used for all image processing devices/modalities. This invention uses a universal platform to provide a generalized medical image processing system which handles different types of medical image apparatuses (modalities) on a single data processing platform. Along these lines, the invention allows the processing platform to be shared among all image acquisition apparatuses, such as mammography, X-ray, CT Scan, MRI, two-photon and laser microscopy, digital pathology, etc. The invention also allows the processing platform to deliver images to a variety of client devices, such as a desktop computer or a handheld device, without high-performance graphical display capabilities because the rendering of the images is performed on the universal platform of the invention.

A first aspect of the present invention provides a universal image processing method, comprising: acquiring image data in a processing system from an imaging device, the imaging device being one of a plurality of imaging devices with which the processing system is configured to communicate; and prefiltering the image data; reconstructing an image from the image data; analyzing the image; providing feedback to the imaging device in response to at least one of the reconstructing and the analyzing; and visualizing the image on a display device, the display device being one of a plurality of display devices with which the processing system is configured to communicate.

A second aspect of the present invention provides a universal image processing system, comprising: a module for acquiring image data in a processing system from an imaging device, the imaging device being one of a plurality of imaging devices with which the processing system is configured to communicate; a module for prefiltering the image data; a module for reconstructing an image from the image data; a module for analyzing the image; a module for providing feedback to the imaging device; and a module for visualizing the image.

A third aspect of the present invention provides a program product stored on a computer readable medium for universally processing an image, the program product comprising program code for causing a computer system to: acquire image data in a processing system from an imaging device, the imaging device being one of a plurality of imaging devices with which the processing system is configured to communicate; and prefilter the image data; reconstruct an image from the image data; analyze the image; provide feedback to the imaging device; and visualize the image.

A fourth aspect of the present invention provides a method for deploying a system for universally processing an image, comprising: providing a computer infrastructure being operable to: acquire image data in a processing system from an imaging device, the imaging device being one of a plurality of imaging devices with which the processing system is configured to communicate; and prefilter the image data; reconstruct an image from the image data; analyze the image; provide feedback to the imaging device; and visualize the image.

A fifth aspect of the present invention provides computer software embodied in a propagated signal for universally processing an image, the computer software comprising instructions for causing a computer system to: acquire image data in a processing system from an imaging device, the imaging device being one of a plurality of imaging devices with which the processing system is configured to communicate; and prefilter the image data; reconstruct an image from the image data; analyze the image; provide feedback to the imaging device; and visualize the image.

A sixth aspect of the present invention provides a data processing system for universally processing an image, the data processing system comprising: a memory medium, a bus coupled to the memory medium; and a processor coupled to the bus, the memory medium comprising instructions that when executed by the processor cause the data processing system to: acquire image data from an imaging device, the imaging device being one of a plurality of imaging devices with which the processing system is configured to communicate; and prefilter the image data; reconstruct an image from the image data; analyze the image; provide feedback to the imaging device; and visualize the image.

Each of these aspects also provides one or more of the following additional aspects: the acquiring, the prefiltering, the reconstructing, the analyzing, and the providing of the feedback can be performed by the processing system; the image data can be temporarily stored before the reconstructing and/or permanently stored after the reconstructing; the feedback can be used to enhance at least one of the acquiring and the prefiltering; the imaging device can first be initialized and calibrated; the image can be previewed, registering and/or mapped; and the image data can be prepared and tailored for display on a particular display device.

BRIEF DESCRIPTION OF THE DRAWINGS

These and other features of this invention will be more readily understood from the following detailed description of the various aspects of the invention taken in conjunction with the accompanying drawings in which.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

For convenience purposes, the Detailed Description of the Invention has the following sections:
  I. General Description
  II. Computerized Implementation I. General Description Medical Imaging is a broad, complex market providing an in-vivo and non-invasive lens through which to explore, evaluate, visualize, and interpret the information associated with the multifaceted structures and dynamic processes in healthy and sick tissues, and organs. It is maturing from the role of an important diagnostic support service to an even more significant fundamental and diverse role in global healthcare. Medical Imaging considers the patient in time, space, and context, from an anatomical view down to the molecular level, in tune with the developments of the "post-genomic era." These technologies when applied to areas ranging from cell and molecular biology to radiology, pathology, surgery, and physiology, will allow a more comprehensive understanding of and better care of the mind and body. New medical, molecular and radioisotope imaging methods reflect anatomy and dynamic body functions heretofore discerned only from hand-drawn textbook illustrations.

These new methods give functional images of blood flow, tumor identification, drug performance, and metabolism essential in the brain, heart, liver, stomach, kidneys, bone, and other organs. Many of today's medical imaging scanners are tomography-based; they take a number, anywhere between 16 and 1000, of two-dimensional images called "slices". Using a sophisticated computer algorithm the 2D slices, from the same modality (same patient at different times) or different modalities (i.e., PET and MRI), can be combined, or fused, into a single 3D image which can be rotated and translated to visualize the object that was scanned. The followings are some of medical image technologies:

(1) Emission-based tomography methods—PET, SPECT. These are an important part of molecular imaging—they are used mostly for brain, heart, and lung scans.

(2) Optical technologies—Fluorescence, digital microscopy, and Optical coherence tomography (OCT).

(3) Structural imaging methods—X-ray, CT, MRI, and Ultrasound—these are useful to provide an anatomical frame of reference onto which other molecular imaging scans can be transposed.

(4) Functional methods—fMRI is a technique for determining which parts of the brain are activated by different types of physical sensation or activity, such as sight, sound, or the movement of a subject's fingers.

Practically every medical imaging scanner purchased today comes with at least one dedicated computer system to manage the scanner and to analyze the raw image data. It is not uncommon for large hospitals, pharmaceutical companies and medical schools to have many imaging scanners in a single building. For example, a large hospital may have several MRI scanners with different strength magnets and bore sizes, PET, CT, Ultrasound, and X-ray systems. The computers associated with these scanners are dedicated and not shared between the different modalities even if one system is underutilized while a system down the hall cannot keep up with the computational demands being put on it.

Most new PET, CT and MRI scanners are configured with multiple collectors and the data is collected in parallel in 2D planes or 3D volumes. Modern parallel imaging methods have significantly reduced image acquisition time from about an hour down to several minutes or seconds. However, the large computational requirements associated with parallel imaging require new, efficient reconstruction processing. This implementation does not allow the computing resource to be shared with other applications and therefore the utilization of such a system is very low.

This invention, a universal medical image processing system, overcomes these problems and opens up a new way of processing medical images more efficiently. The invention allows the image processing platform to be shared among all image acquisition modalities such as mammography, X-ray, CT, PET, SPECT and MRI.

As indicated above, the present invention provides a universal and centralized image (e.g., medical, bio-molecular, etc.) processing system platform. The invention permits sharing both computation and visualization across a single universal platform, thus allowing for sharing of computing resources and visualization of images on a variety of imaging (client) devices without high-performance graphical display cards. In a typical embodiment a (e.g., medical) image 2D linear registration algorithm is implemented on a Cell Broadband Engine processor, which has nine processor cores on a chip and has a 4-way SIMD unit for each core.

By exploiting a highly parallel architecture and a high memory bandwidth of the Cell Broadband Engine architecture, this implementation with two Cell Broadband Engine processors can compute mutual information for about 33 million pixel pairs in a second. This technological advancement allows for the development of an image processing system that can be used for all image processing devices/modalities. This invention uses a universal platform to provide a generalized medical image processing system which handles different types of medical image apparatuses (modalities) on a single data processing platform. Along these lines, the invention allows the processing platform to be shared among all image acquisition apparatuses, such as mammography, X-ray, CT Scan, MRI, two-photon and laser microscopy, digital pathology, etc. The invention also allows the processing platform to deliver images to a variety of client devices, such as a desktop computer or a handheld device, without high-performance graphical display capabilities because the rendering of the images is performed on the universal platform of the invention.

It should be understood in advance that although this disclosure describes the invention with respect to medial imaging, the teachings described herein could be applied to any other technology such as document scanning, photographs, etc.

Figure 1:
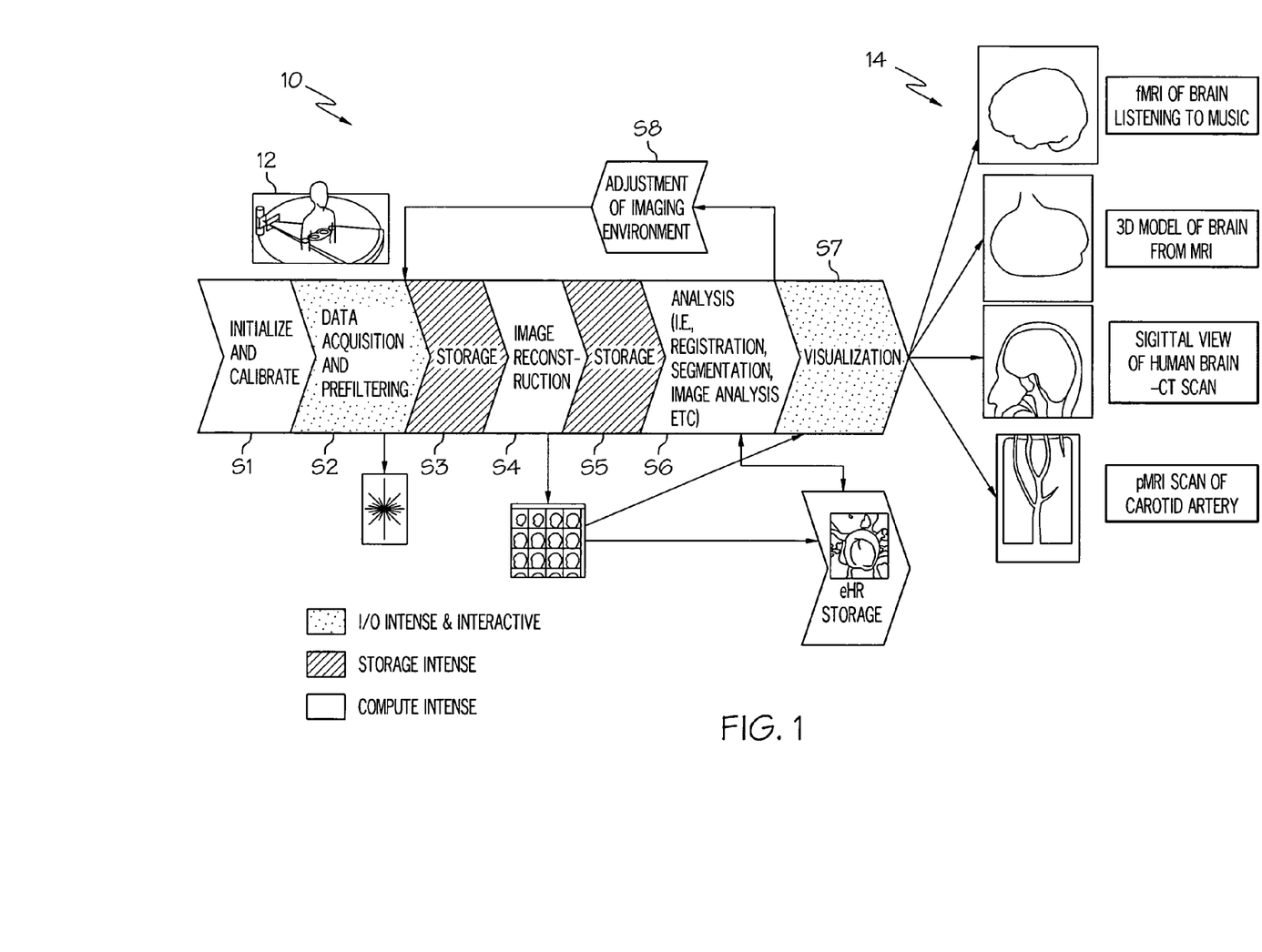
FIG. 1 shows a universal image processing workflow according to the present invention.

Referring now to FIG. 1 an image processing flow 10 according to the present invention is shown. As depicted, the imaging device 12 is initialized and calibrated in step S1. Along these lines, the present invention is especially advantageous because it is configured to communicate with multiple imaging devices. Specifically, the system of the present invention can communicate with any type (e.g., NMR, CT, desktop scanner, camera) of imaging device 12. Previous systems were local or specifically assigned to a particular imaging device. In any event, in step S2, image data is acquired from imaging device 12 and is prefiltered. At step S3, the image data can be temporarily stored for image reconstruction in step S4. The reconstructed image can then be stored in step S5 for analysis in step S6. Such analysis can include, among other things, registration and segmentation. After analysis, the image can be visualized in step S7 and a display 14 corresponding to imaging device 12. Thus, the present invention is also configured to communicate with any number of display devices.

Under the present invention feedback can also be generated and provided to imaging device 12. Specifically, as shown in step S8, the imaging environment can be adjusted based on the steps up through analysis 56. The feedback can also be used to enhance the data acquisition and prefiltering.

Figure 2:
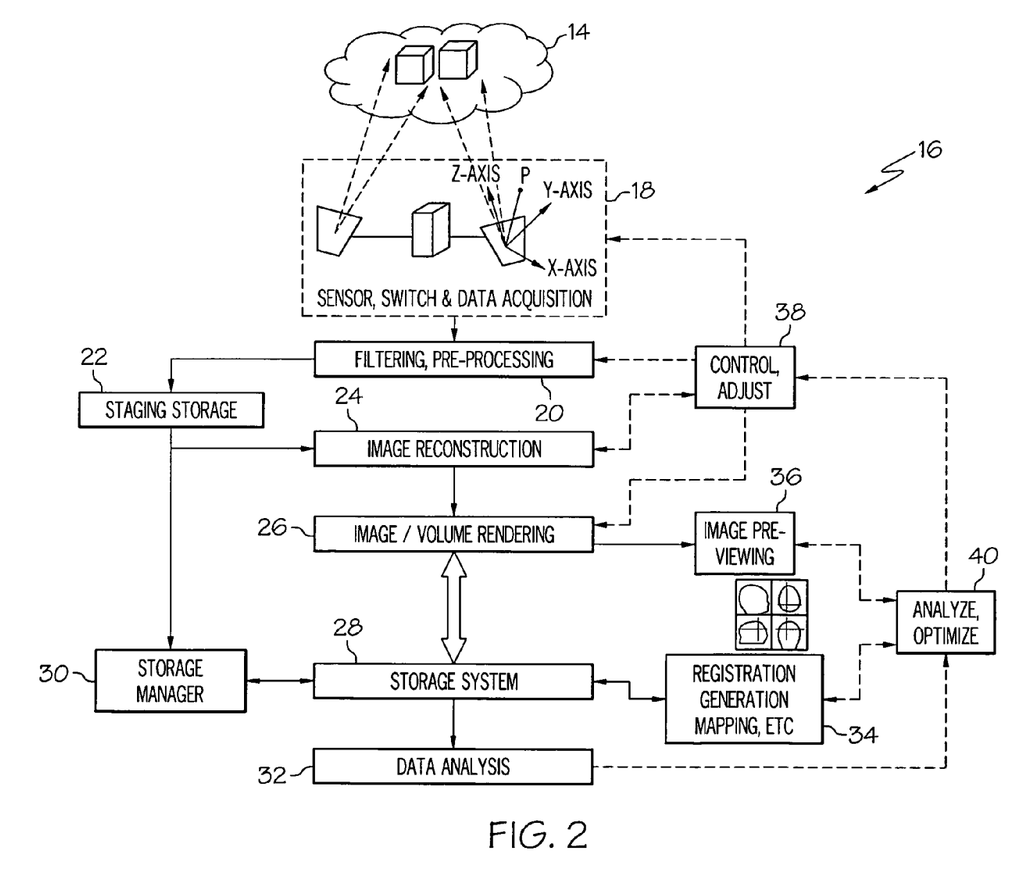
FIG. 2 shows a universal processing system according to the present invention.

Referring now to FIG. 2, these concepts are depicted in a system view 16 of the invention. In general, system 16 comprises the following modules:

Data acquisition module 18 having imaging device/modality 14 specific sensors, switch & data acquisition capabilities. As shown, system 16 is configured to communicate with multiple different types of imaging devices 14.

Filtering and preprocessing module 20 for prefiltering any artifacts or "noise" from the image data.

Staging storage 22 for providing temporary storage for the image data.

Image reconstruction module 24 for reconstructing an image from the image data stored in staging storage 22. Reconstruction algorithms are specific to each modality and there are many different algorithms for each. The algorithms typically employ some type of inverse transform such as Radon (PET) and FFT (MRI) or matrix inversion. The computational complexity of these algorithms can range from simple for 2D FFT to very complex for large matrix inversions. They can take anywhere from several minutes to tens of hours on a high-end desktop PC. Device/modality vendors usually include an image reconstruction application when the customer purchases their scanner.

Image/volume rendering module 26 for rendering the image on a display.

Image pre-viewing module 36 for providing a preview of the image if desired.

Storage system 28 and manager 30 for providing permanent storage for the image/image data.

Registration and mapping module 34 for registering and mapping the image.

Data processing and analysis module 32 for processing and analyzing the image/image data.

Analysis and optimization module 40 for optimizing the image/image data based on the analysis. This could include, among other things, eliminating additional artifacts. Analysis could include image registration (fusion), segmentation, and knowledge extraction (also know as feature detection, extraction and identification). Image analysis phases can be very computer intensive. The results of these phases are then stored along with the image in the central repository. Registration is the aligning or developing of correspondences between data from different modalities, such as PET and CT in order to combine the information contained in both or within the same modality as in MRI images for a single patient at different times. MRI scans for a patient are taken over a period of time, maybe once a month for 6 to 8 months. The images are fused together to give the doctor or research a view of the progress, or lack of progress, of the drug in question. Segmentation is the process of identifying and classifying data found in a digitally sampled representation. An example would be labeling and measuring the different features in a 3D MRI of a human brain. Visualization can be done after image reconstruction and image analysis. It is usually performed with a high-resolution graphics card in a desktop PC or workstation. Knowledge extraction involves searching and analysis of images in order to generate additional and/or new information that can be use by physicians, researchers, and other medical professionals. The new information may be combined with data from other sources such as genomics, proteomics and immunological data to help the physician make more informed and better decisions. The Cell BE multicore processing technology allows massive parallel image processing in a medical clinical application.

Feedback control and adjustment module 38 is for generating and providing the above-mentioned feedback to the respective imaging devices 14.

Although not shown, processing system 16 and/or imaging devices 14 can include an image transcoding, streaming, and display module. For example, once an image is ready to be viewed, it must be prepared for display on a client device. Some client devices, such as a desktop PC, have graphical display cards that are capable of rendering and displaying medical images. However, some devices, such as a web browser or handheld device, do not have the capability of rendering and displaying high-resolution medical images. Thus, it is necessary to render the images on the universal platform and then stream them to the client device. The streaming of an image must be transcoded, or tailored, to fit the display capabilities of each client device. In general, processing system 16 allows an image processing system to be shared, controlled, adjusted and optimized among all imaging devices/modalities and image analysis applications, and to deliver images to a variety of client devices.

The data collection phase is typically device/modality dependent and can take anywhere from minutes to hours. After the patient/specimen is scanned, the image can be generated using a modality dependent image reconstruction algorithm, and visualized. For each modality, there are a number of algorithms for image reconstruction. The algorithms typically employ an (inverse) FFT or matrix inversion phase and can be very computationally expensive. In some cases, this step can take several hours on a desktop PC.

Figure 3:
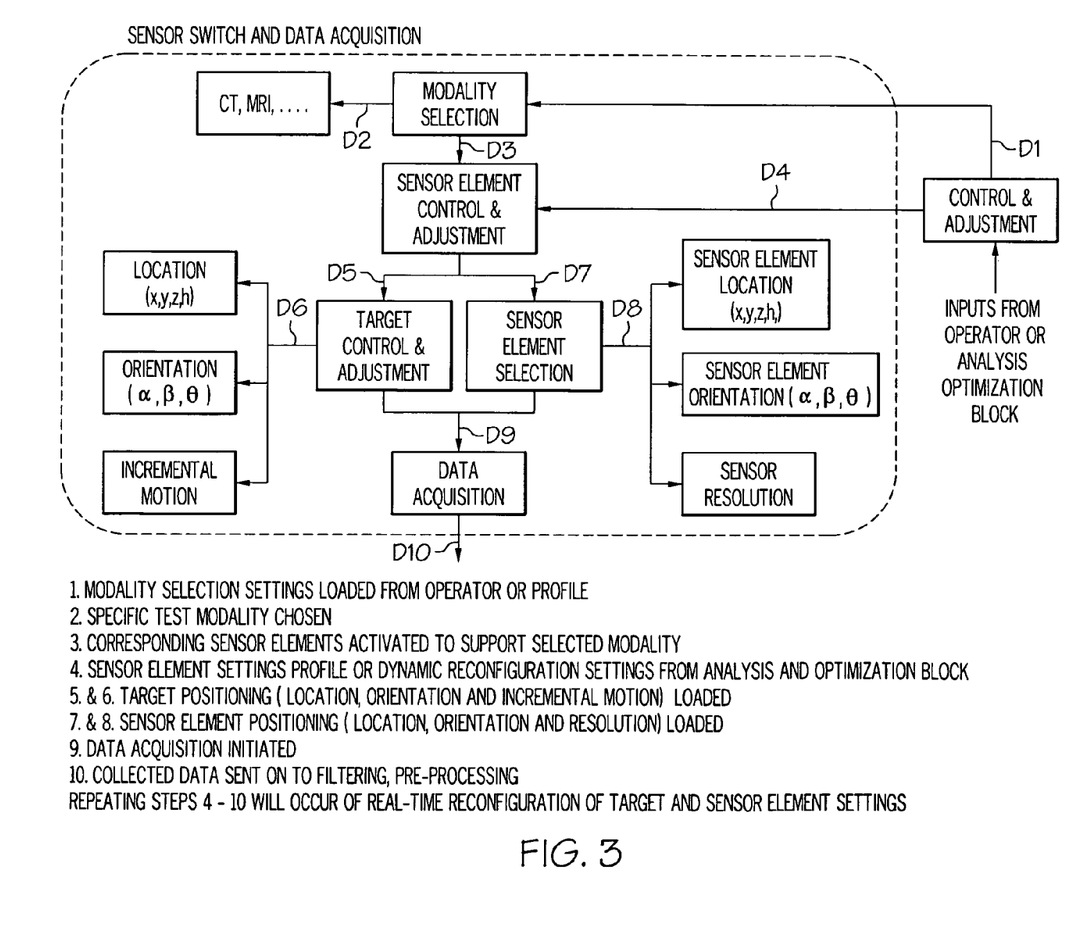
FIG. 3 shows an image data acquisition process flow according to the present invention.

Referring to FIG. 3, a data acquisition process flow according to the present invention is shown. In step D1, device/modality selection settings are loaded from an operator or profile. In step D2, a specific test device/modality is chosen. In step D3, corresponding sensor elements are activated to support the selected device/modality. In step D4, sensor element settings are determined for the analysis and optimization discussed above. In steps D5 and D6, target position (location, orientation, and incremental motion) settings are loaded. In step D7 and D8, sensor element positioning (location, orientation and resolution) settings are loaded. In step D9, data acquisition is initiated, and in Step D10, collected data is sent along to preprocessing and prefiltering. It should be noted that steps D4-D10 can be repeated in real-time.

Figure 4:
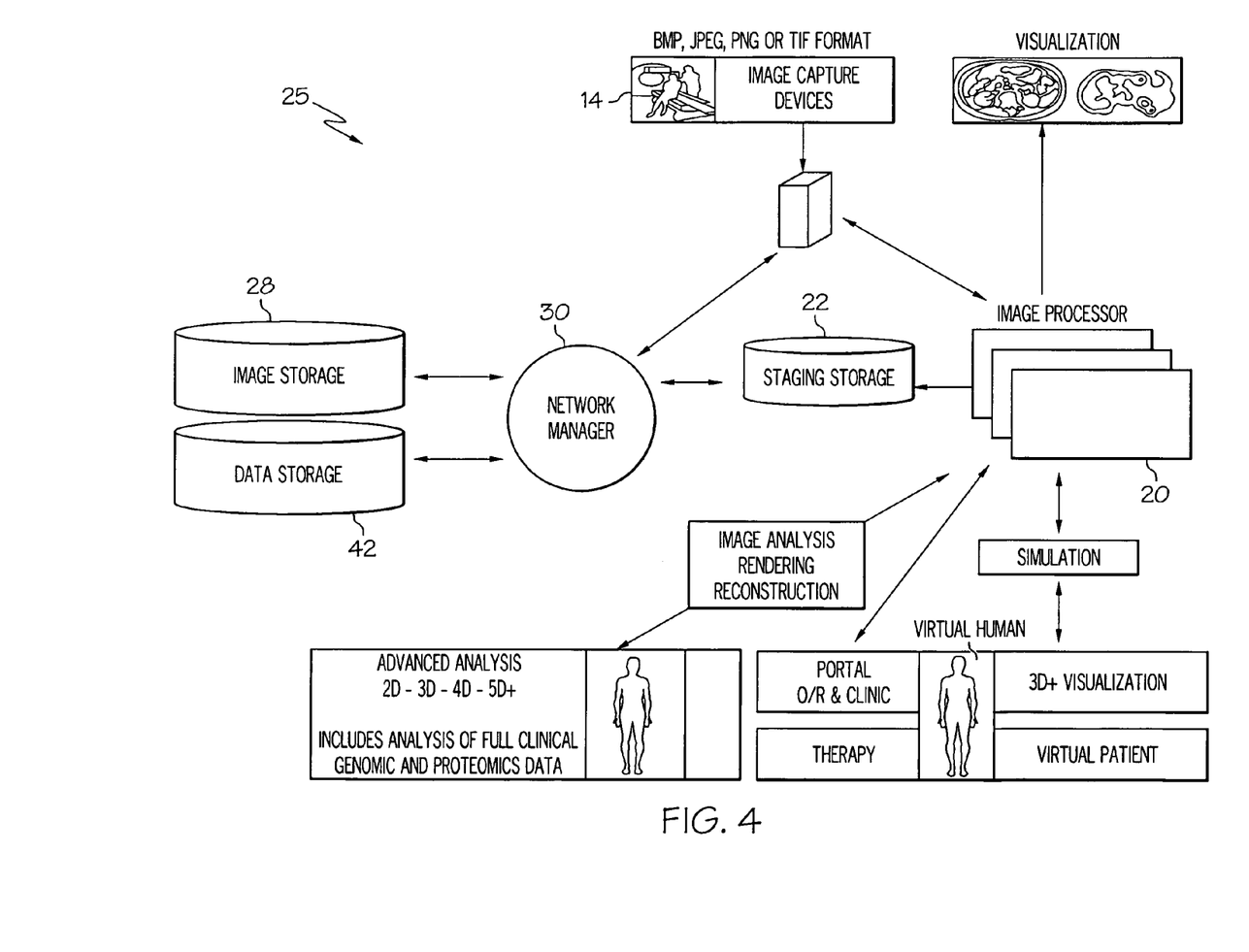
FIG. 4 shows an image data storage architecture according to the present invention.

Referring now to FIG. 4, an image data storage architecture 25 according to the present invention is shown. As described above, image data is acquired for an imaging device 14 and processed/pre-filtered by prefiltering module 20, after which the image data can be temporarily stored in staging storage system 22. After the image is reconstructed, it can be permanently stored by network manager 30 in image storage system 28. Similarly the corresponding image data can be stored in data storage system 42. Aside from the storage options shown in FIG. 4, the present invention will perform any addition operations described above such as image analysis, rendering and reconstruction, simulation, etc.

Figure 5:
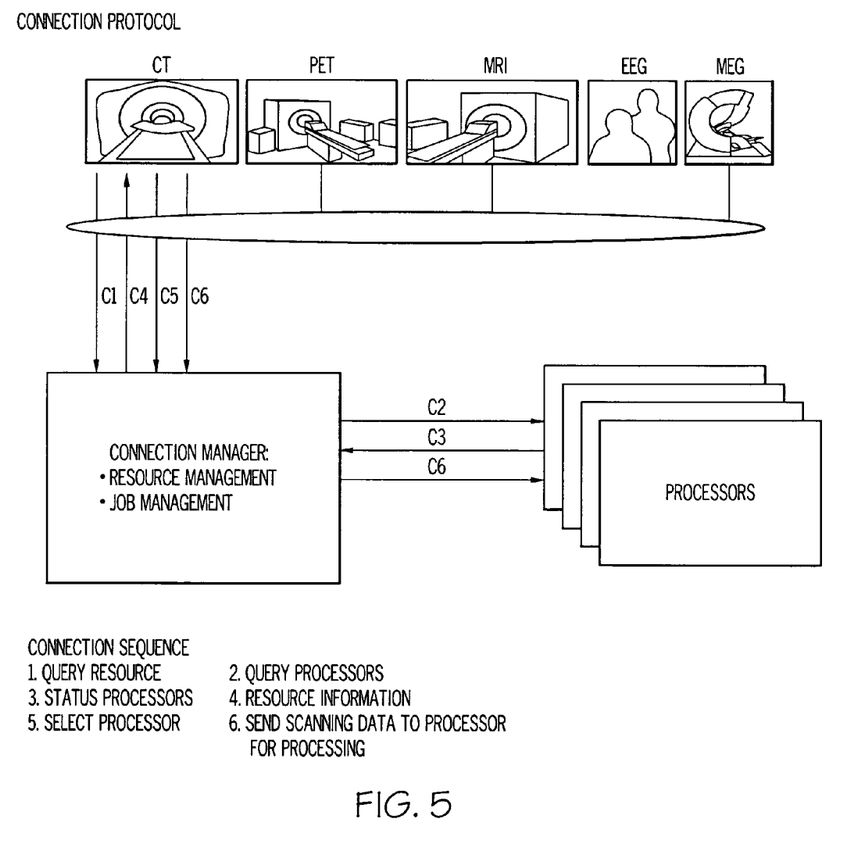
FIG. 5 shows a diagram of a connection protocol according to the present invention.

FIG. 5 shows a diagram of a connection protocol according to the present invention. When a device/modality initiates image scanning, it sends a signal to the connection manager by querying the resources and the connection sequence as follows. The scanning is done in parallel. The connection sequence is as follows: In step C1, the resource is queried. In step C2 the processors are queried. In step C3, the status of processors is determined based on the querying. In step C4, a particular device is selected. In step C5, a processor is selected. In step C6 scanning data is sent to the selected processor for processing.

Figure 6:
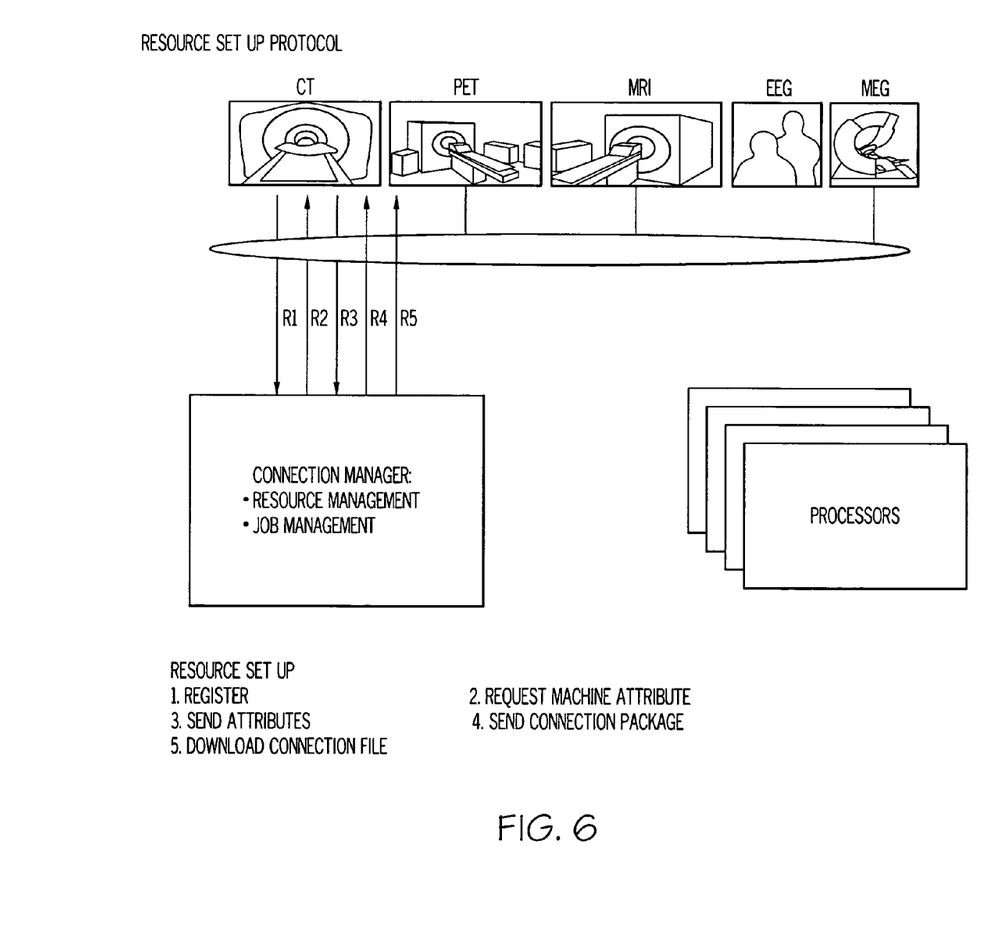
FIG. 6 shows a diagram of a resource set up protocol according to the present invention.

FIG. 6 shows a diagram of a resource set up protocol for a new imaging device or device type according to the present invention. Specifically, when a new device/modality is brought in to the system, the set up sequence is as follows: In step R1, the resource is registered. In step R2, a machine attribute is requested. In step R3, the attributes are sent from the imaging device. In step R4 a connection package is sent back to the imaging device. In step R5, a connection file is then downloaded to the imaging device.

Figure 7:
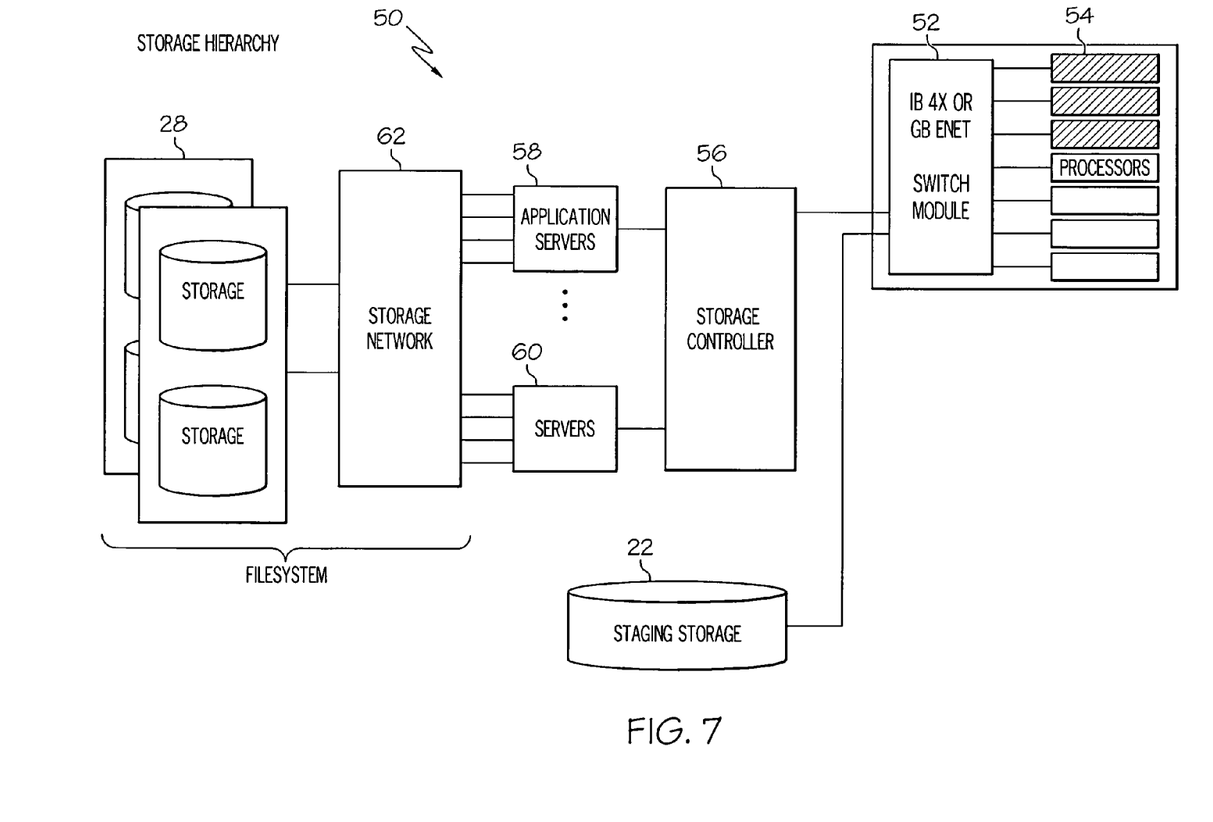
FIG. 7 shows a diagram of a storage hierarchy according to the present invention.

FIG. 7 shows a diagram of a storage hierarchy 50 according to the present invention. In general, the medical image scanning data rate is several GB per second. Therefore, it typically requires a staging storage system 22 to process image data. This image can be viewed to determine the quality of image, and it can be rescanned if the image is poor. The scanned image is permanently stored to the storage farm 28 via a network such as a SAN or a storage grid. In any event, switch module 52 works in conjunction with processors 54 provide an image to storage controller 56, which can store image data in staging storage 22, or a reconstructed image in storage farm 28. In the case of the latter, storage controller 56 will communicate with application servers 58 and/or servers 60 to access storage network 62.

II. Computerized Implementation

Figure 8:
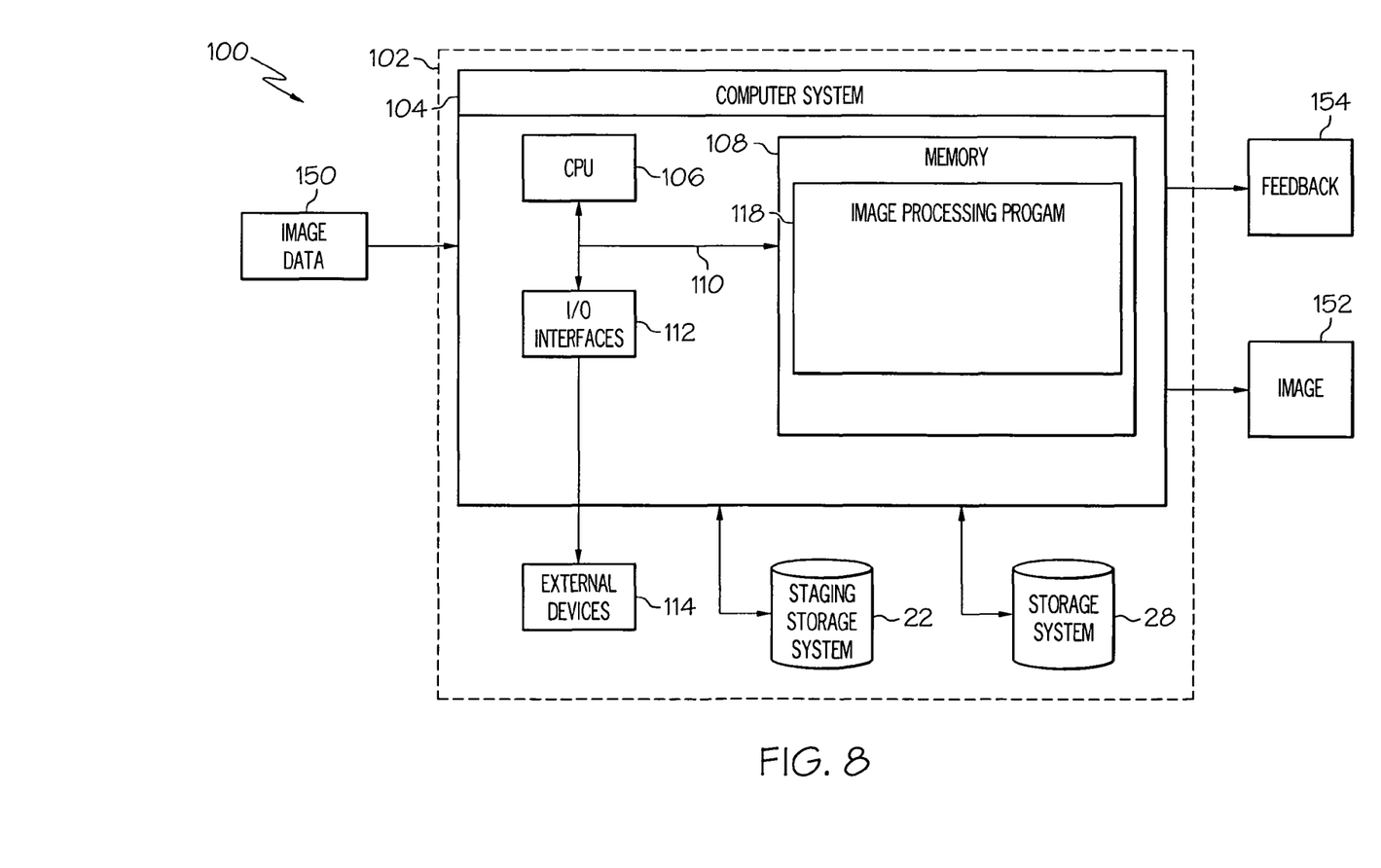
FIG. 8 shows a diagram of a computerized implementation according to the present invention.

Referring now to FIG. 8, a more detailed diagram of a computerized implementation 100 of the present invention is shown. As depicted, implementation 100 includes computer system 104 deployed within a computer infrastructure 102. This is intended to demonstrate, among other things, that the present invention could be implemented within a network environment (e.g., the Internet, a wide area network (WAN), a local area network (LAN), a virtual private network (VPN), etc.), or on a stand-alone computer system. In the case of the former, communication throughout the network can occur via any combination of various types of communications links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer infrastructure 102 is intended to demonstrate that some or all of the components of implementation 100 could be deployed, managed, serviced, etc. by a service provider who offers to implement, deploy, and/or perform the functions of the present invention for others.

As shown, computer system 104 includes a processing unit 106, a memory 108, a bus 110, and input/output (I/O) interfaces 112. Further, computer system 104 is shown in communication with external I/O devices/resources 114 and storage systems 22 and 28. In general, processing unit 106 executes computer program code, such as image processing program 118, which is stored in memory 108 and/or storage system 106. While executing computer program code, processing unit 106 can read and/or write data to/from memory 18, storage system 106, and/or I/O interfaces 112. Bus 110 provides a communication link between each of the components in computer system 104. External devices 114 can comprise any devices (e.g., keyboard, pointing device, display, etc.) that enable a user to interact with computer system 104 and/or any devices (e.g., network card, modem, etc.) that enable computer system 104 to communicate with one or more other computing devices.

Computer infrastructure 102 is only illustrative of various types of computer infrastructures for implementing the invention. For example, in one embodiment, computer infrastructure 102 comprises two or more computing devices (e.g., a server cluster) that communicate over a network to perform the process(es) of the invention. Moreover, computer system 104 is only representative of various possible computer systems that can include numerous combinations of hardware. To this extent, in other embodiments, computer system 14 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively. Moreover, processing unit 106 may comprise a single processing unit, or be distributed across one or more processing units in one or more locations, e.g., on a client and server. Similarly, memory 108 and/or storage systems 22 and 28 can comprise any combination of various types of data storage and/or transmission media that reside at one or more physical locations. Further, I/O interfaces 112 can comprise any system for exchanging information with one or more external device 114. Still further, it is understood that one or more additional components (e.g., system software, math co-processing unit, etc.) not shown in FIG. 1 can be included in computer system 104. However, if computer system 104 comprises a handheld device or the like, it is understood that one or more external devices 114 (e.g., a display) and/or storage systems 22 and 28 could be contained within computer system 104, not externally as shown.

Storage systems 22 and 28 can be any type of systems (e.g., a databases) capable of providing storage for information under the present invention. To this extent, storage systems 22 and 28 could include one or more storage devices, such as a magnetic disk drive or an optical disk drive. In another embodiment, storage systems 22 and 28 include data distributed across, for example, a local area network (LAN), wide area network (WAN) or a storage area network (SAN) (not shown). In addition, although not shown, additional components, such as cache memory, communication systems, system software, etc., may be incorporated into computer system 104.

Shown in memory 108 of computer system 104 is image processing program 118, which facilitates the functions as described herein. Specifically, image processing program 118 should be understood to contain one or more of the modules depicted in FIG. 2, whose functions are also described in FIG. 1. For example, image data 150 is acquired, processed, analyzed, etc., an image 152 is output as well as feedback 154 for improving the process.

While shown and described herein as a method and system for processing an image, it is understood that the invention further provides various alternative embodiments. For example, in one embodiment, the invention provides a computer-readable/useable medium that includes computer program code to enable a computer infrastructure to process an image. To this extent, the computer-readable/useable medium includes program code that implements the process(es) of the invention. It is understood that the terms computer-readable medium or computer useable medium comprises one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory 18 (FIG. 8) and/or storage system 16 (FIG. 8) (e.g., a fixed disk, a read-only memory, a random access memory, a cache memory, etc.), and/or as a data signal (e.g., a propagated signal) traveling over a network (e.g., during a wired/wireless electronic distribution of the program code).

In another embodiment, the invention provides a business method that performs the process of the invention on a subscription, advertising, and/or fee basis. That is, a service provider, such as a Solution Integrator, could offer to transition an organization to an IT service management-oriented organization. In this case, the service provider can create, maintain, support, etc., a computer infrastructure, such as computer infrastructure 102 (FIG. 8) that performs the process of the invention for one or more customers. In return, the service provider can receive payment from the customer(s) under a subscription and/or fee agreement and/or the service provider can receive payment from the sale of advertising content to one or more third parties.

In still another embodiment, the invention provides a computer-implemented method for processing an image. In this case, a computer infrastructure, such as computer infrastructure 102 (FIG. 8), can be provided and one or more systems for performing the process of the invention can be obtained (e.g., created, purchased, used, modified, etc.) and deployed to the computer infrastructure. To this extent, the deployment of a system can comprise one or more of: (1) installing program code on a computing device, such as computer system 104 (FIG. 8, from a computer-readable medium; (2) adding one or more computing devices to the computer infrastructure; and (3) incorporating and/or modifying one or more existing systems of the computer infrastructure to enable the computer infrastructure to perform the process of the invention.

As used herein, it is understood that the terms "program code" and "computer program code" are synonymous and mean any expression, in any language, code or notation, of a set of instructions intended to cause a computing device having an information processing capability to perform a particular function either directly or after either or both of the following: (a) conversion to another language, code or notation; and/or (b) reproduction in a different material form. To this extent, program code can be embodied as one or more of: an application/software program, component software/a library of functions, an operating system, a basic I/O system/driver for a particular computing and/or I/O device, and the like.

A data processing system suitable for storing and/or executing program code can be provided hereunder and can include at least one processor communicatively coupled, directly or indirectly, to memory element(s) through a system bus. The memory elements can include, but are not limited to, local memory employed during actual execution of the program code, bulk storage, and cache memories that provide temporary storage of at least some program code in order to reduce the number of times code must be retrieved from bulk storage during execution. Input/output or I/O devices (including, but not limited to, keyboards, displays, pointing devices, etc.) can be coupled to the system either directly or through intervening I/O controllers.

Network adapters also may be coupled to the system to enable the data processing system to become coupled to other data processing systems, remote printers, storage devices, and/or the like, through any combination of intervening private or public networks. Illustrative network adapters include, but are not limited to, modems, cable modems and Ethernet cards.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

We claim:

1. A universal image processing method, comprising:
    acquiring image data in a processing system from an imaging device, the imaging device being one of a plurality of imaging devices with which the processing system is configured to communicate; and
    prefiltering the image data;
    reconstructing an image from the image data;
    analyzing the image;
    providing feedback to the imaging device in response to at least one of the reconstructing and the analyzing; and
    visualizing the image on a display device, the display device being one of a plurality of display devices with which the processing system is configured to communicate.

2. The method of claim 1, the acquiring, the prefiltering, the reconstructing, the analyzing, and the providing being performed by the processing system.

3. The method of claim 1, further comprising temporarily storing the image data before the reconstructing.

4. The method of claim 1, further comprising permanently storing the image data after the reconstructing.

5. The method of claim 1, further comprising using the feedback to enhance at least one of the acquiring and the prefiltering.

6. The method of claim 1, further comprising initializing and calibrating the imaging device.

7. The method of claim 1, further comprising:
previewing the image;
registering and mapping the image; and
preparing and tailoring the image data for specific display on the display device.

8. A universal image processing system, comprising:
a module for acquiring image data in a processing system from an imaging device, the imaging device being one of a plurality of imaging devices with which the processing system is configured to communicate; and
a module for prefiltering the image data;
a module for reconstructing an image from the image data;
a module for analyzing the image;
a module for providing feedback to the imaging device; and
a module for visualizing the image.

9. The system of claim 8, further comprising a module for temporarily storing the image data before the reconstructing.

10. The system of claim 8, further comprising a module for permanently storing the image data after the reconstructing.

11. The system of claim 8, further comprising using the feedback to enhance at least one of the acquiring and the prefiltering.

12. The system of claim 8, further comprising a module for registering and mapping the image.

13. The system of claim 8, further comprising a module for previewing the image.

14. A program product stored on a computer readable medium for universally processing an image, the program product comprising program code for causing a computer system to:
acquire image data in a processing system from an imaging device, the imaging device being one of a plurality of imaging devices with which the processing system is configured to communicate; and
prefilter the image data;
reconstruct an image from the image data;
analyze the image;
provide feedback to the imaging device; and
visualize the image.

15. The program product of claim 14, the program product further comprising program code for causing the computer system to temporarily store the image data before the reconstructing.

16. The program product of claim 14, the program product further comprising program code for causing the computer system to permanently store the image data after the reconstructing.

17. The program product of claim 14, the program product further comprising program code for causing the computer system to use the feedback to enhance at least one of the acquiring and the prefiltering.

18. The program product of claim 14, the program product further comprising program code for causing the computer system to initialize and calibrate the imaging device.

19. The program product of claim 14, the program product further comprising program code for causing the computer system to:
preview the image; and
register and mapping the image.

20. A method for deploying a system for universally processing an image, comprising:
providing a computer infrastructure being operable to:
acquire image data in a processing system from an imaging device, the imaging device being one of a plurality of imaging devices with which the processing system is configured to communicate; and
prefilter the image data;
reconstruct an image from the image data;
analyze the image;
provide feedback to the imaging device; and
visualize the image.

* * * * *